United States Patent
Mountain

(10) Patent No.: US 9,511,259 B2
(45) Date of Patent: Dec. 6, 2016

(54) FITNESS OVERLAY AND INCORPORATION FOR HOME AUTOMATION SYSTEM

(71) Applicant: ECHOSTAR UK HOLDINGS LIMITED, Keighley (GB)

(72) Inventor: Dale Llewelyn Mountain, Keighley (GB)

(73) Assignee: ECHOSTAR UK HOLDINGS LIMITED (GB)

( * ) Notice: Subject to any disclaimer, the term of this patent is extended or adjusted under 35 U.S.C. 154(b) by 0 days.

(21) Appl. No.: 14/528,739

(22) Filed: Oct. 30, 2014

(65) Prior Publication Data

US 2016/0121161 A1    May 5, 2016

(51) Int. Cl.
*A63B 24/00* (2006.01)
*G01K 13/00* (2006.01)
*F24F 11/00* (2006.01)
*G06F 19/00* (2011.01)

(52) U.S. Cl.
CPC ....... *A63B 24/0062* (2013.01); *A63B 24/0087* (2013.01); *F24F 11/0012* (2013.01); *G01K 13/00* (2013.01); *G06F 19/3481* (2013.01); *A63B 2024/0065* (2013.01)

(58) Field of Classification Search
CPC . A63B 24/00; A63B 24/0062; A63B 24/0087; A63B 2024/0065; G01K 13/00; F24F 11/0012; G06F 19/3481
See application file for complete search history.

(56) References Cited

U.S. PATENT DOCUMENTS

| | | |
|---|---|---|
| 4,386,436 A | 5/1983 | Kocher et al. |
| 4,581,606 A | 4/1986 | Mallory |
| 4,728,949 A | 3/1988 | Platte et al. |
| 4,959,713 A | 9/1990 | Morotomi et al. |
| 5,400,246 A | 3/1995 | Wilson et al. |
| 5,770,896 A | 6/1998 | Nakajima |
| 5,805,442 A | 9/1998 | Crater et al. |
| 5,822,012 A | 10/1998 | Jeon et al. |
| 5,926,090 A | 7/1999 | Taylor et al. |
| 5,970,030 A | 10/1999 | Dimitri et al. |
| 6,081,758 A | 6/2000 | Parvulescu |
| 6,104,334 A | 8/2000 | Allport |

(Continued)

FOREIGN PATENT DOCUMENTS

| | | |
|---|---|---|
| CA | 2 267 988 A1 | 4/1998 |
| EP | 2 736 027 A1 | 5/2014 |

(Continued)

OTHER PUBLICATIONS

"Acoustic/Ultrasound Ultrasonic Flowmeter Basics," Questex Media Group LLC, accessed on Dec. 16, 2014, 4 pages. Retrieved from http://www.sensorsmag.com/sensors/acoustic-ultrasound/ultrasonic-flowmeter-basics-842.

(Continued)

*Primary Examiner* — Glenn Richman
(74) *Attorney, Agent, or Firm* — Kilpatrick Townsend & Stockton LLP

(57) ABSTRACT

Systems and methods for displaying fitness information with an electronic device may include receiving multimedia content at an input of the electronic device. The electronic device may provide the audiovisual content to a display device. The electronic device may also receive fitness information, and may provide this fitness information to the display device.

9 Claims, 6 Drawing Sheets

(56) References Cited

U.S. PATENT DOCUMENTS

| | | |
|---|---|---|
| 6,182,094 B1 | 1/2001 | Humpleman et al. |
| 6,330,621 B1 | 12/2001 | Bakke et al. |
| 6,377,858 B1 | 4/2002 | Koeppe |
| 6,405,284 B1 | 6/2002 | Bridge |
| 6,502,166 B1 | 12/2002 | Cassidy |
| 6,529,230 B1 | 3/2003 | Chong |
| 6,553,375 B1 | 4/2003 | Huang et al. |
| 6,662,282 B2 | 12/2003 | Cochran |
| 6,756,998 B1 | 6/2004 | Bilger |
| 6,976,187 B2 | 12/2005 | Arnott et al. |
| 6,989,731 B1 | 1/2006 | Kawai et al. |
| 7,009,528 B2 | 3/2006 | Griep |
| 7,088,238 B2 | 8/2006 | Karaoguz et al. |
| 7,143,298 B2 | 11/2006 | Wells et al. |
| 7,234,074 B2 | 6/2007 | Cohn et al. |
| 7,346,917 B2 | 3/2008 | Gatto et al. |
| 7,372,370 B2 | 5/2008 | Stults et al. |
| 7,386,666 B1 | 6/2008 | Beauchamp et al. |
| 7,395,369 B2 | 7/2008 | Sepez et al. |
| 7,395,546 B1 | 7/2008 | Asmussen |
| 7,574,494 B1 | 8/2009 | Mayernick et al. |
| 7,590,703 B2 | 9/2009 | Cashman et al. |
| 7,640,351 B2 | 12/2009 | Reckamp et al. |
| 7,694,005 B2 | 4/2010 | Reckamp et al. |
| 7,739,718 B1 | 6/2010 | Young et al. |
| 7,861,034 B2 | 12/2010 | Yamamoto et al. |
| 7,870,232 B2 | 1/2011 | Reckamp et al. |
| 7,969,318 B2 | 6/2011 | White et al. |
| 8,086,757 B2 | 12/2011 | Chang |
| 8,106,768 B2 | 1/2012 | Neumann |
| 8,156,368 B2 | 4/2012 | Chambliss et al. |
| 8,171,148 B2 | 5/2012 | Lucas et al. |
| 8,180,735 B2 | 5/2012 | Ansari et al. |
| 8,201,261 B2 | 6/2012 | Barfield et al. |
| 8,221,290 B2 * | 7/2012 | Vincent .............. A63B 24/0021 273/440 |
| 8,289,157 B2 | 10/2012 | Patenaude et al. |
| 8,310,335 B2 | 11/2012 | Sivakkolundhu |
| 8,316,413 B2 | 11/2012 | Crabtree |
| 8,413,204 B2 | 4/2013 | White et al. |
| 8,498,572 B1 | 7/2013 | Schooley et al. |
| 8,516,087 B2 | 8/2013 | Wilson et al. |
| 8,550,368 B2 | 10/2013 | Butler et al. |
| 8,619,136 B2 | 12/2013 | Howarter et al. |
| 8,644,525 B2 | 2/2014 | Bathurst et al. |
| 8,645,327 B2 | 2/2014 | Falkenburg et al. |
| 8,799,413 B2 | 8/2014 | Taylor et al. |
| 8,898,709 B2 | 11/2014 | Crabtree |
| 8,930,700 B2 | 1/2015 | Wielopolski |
| 8,965,170 B1 | 2/2015 | Benea et al. |
| 9,019,111 B1 | 4/2015 | Sloo et al. |
| 9,049,567 B2 | 6/2015 | Le Guen et al. |
| 2002/0019725 A1 | 2/2002 | Petite |
| 2002/0063633 A1 | 5/2002 | Park |
| 2003/0097452 A1 | 5/2003 | Kim et al. |
| 2003/0126593 A1 | 7/2003 | Mault |
| 2003/0133551 A1 | 7/2003 | Kahn |
| 2003/0140352 A1 | 7/2003 | Kim |
| 2003/0201900 A1 | 10/2003 | Bachinski et al. |
| 2004/0019489 A1 | 1/2004 | Funk et al. |
| 2004/0117038 A1 | 6/2004 | Karaoguz et al. |
| 2004/0117843 A1 | 6/2004 | Karaoguz et al. |
| 2004/0121725 A1 | 6/2004 | Matsui |
| 2004/0128034 A1 | 7/2004 | Lenker et al. |
| 2004/0148419 A1 | 7/2004 | Chen et al. |
| 2004/0148632 A1 | 7/2004 | Park et al. |
| 2004/0260407 A1 | 12/2004 | Wimsatt |
| 2004/0266419 A1 | 12/2004 | Arling et al. |
| 2005/0038875 A1 | 2/2005 | Park |
| 2005/0188315 A1 | 8/2005 | Campbell et al. |
| 2005/0200478 A1 | 9/2005 | Koch et al. |
| 2005/0264698 A1 | 12/2005 | Eshleman |
| 2005/0289614 A1 | 12/2005 | Baek et al. |
| 2006/0011145 A1 | 1/2006 | Kates |
| 2006/0087428 A1 | 4/2006 | Wolfe et al. |
| 2006/0136968 A1 | 6/2006 | Han et al. |
| 2006/0143679 A1 | 6/2006 | Yamada et al. |
| 2007/0044119 A1 | 2/2007 | Sullivan et al. |
| 2007/0078910 A1 | 4/2007 | Bopardikar |
| 2007/0129220 A1 | 6/2007 | Bardha |
| 2007/0142022 A1 | 6/2007 | Madonna et al. |
| 2007/0146545 A1 | 6/2007 | Iwahashi |
| 2007/0157258 A1 | 7/2007 | Jung et al. |
| 2007/0192486 A1 | 8/2007 | Wilson et al. |
| 2007/0256085 A1 | 11/2007 | Reckamp et al. |
| 2007/0271518 A1 | 11/2007 | Tischer et al. |
| 2008/0021971 A1 | 1/2008 | Halgas |
| 2008/0022322 A1 | 1/2008 | Grannan et al. |
| 2008/0062258 A1 | 3/2008 | Bentkovski et al. |
| 2008/0062965 A1 | 3/2008 | Silva et al. |
| 2008/0109095 A1 | 5/2008 | Braithwaite et al. |
| 2008/0114963 A1 | 5/2008 | Cannon et al. |
| 2008/0123825 A1 | 5/2008 | Abramson et al. |
| 2008/0140736 A1 | 6/2008 | Jarno |
| 2008/0163330 A1 | 7/2008 | Sparrell |
| 2008/0278635 A1 | 11/2008 | Hardacker et al. |
| 2008/0284905 A1 | 11/2008 | Chuang |
| 2008/0288876 A1 | 11/2008 | Fleming |
| 2008/0297660 A1 | 12/2008 | Shioya |
| 2009/0069038 A1 | 3/2009 | Olague et al. |
| 2009/0138507 A1 | 5/2009 | Burckart et al. |
| 2009/0146834 A1 | 6/2009 | Huang |
| 2009/0165069 A1 | 6/2009 | Kirchner |
| 2009/0167555 A1 | 7/2009 | Kohanek |
| 2009/0190040 A1 | 7/2009 | Watanabe et al. |
| 2009/0249428 A1 | 10/2009 | White et al. |
| 2010/0046918 A1 | 2/2010 | Takao et al. |
| 2010/0122284 A1 | 5/2010 | Yoon et al. |
| 2010/0138007 A1 | 6/2010 | Clark et al. |
| 2010/0138858 A1 | 6/2010 | Velazquez et al. |
| 2010/0146445 A1 | 6/2010 | Kraut |
| 2010/0211546 A1 | 8/2010 | Grohman et al. |
| 2010/0321151 A1 | 12/2010 | Matsuura et al. |
| 2011/0030016 A1 | 2/2011 | Pino et al. |
| 2011/0032423 A1 | 2/2011 | Jing et al. |
| 2011/0093126 A1 | 4/2011 | Toba et al. |
| 2011/0119325 A1 | 5/2011 | Paul et al. |
| 2011/0150432 A1 | 6/2011 | Paul et al. |
| 2011/0156862 A1 | 6/2011 | Langer |
| 2011/0187928 A1 | 8/2011 | Crabtree |
| 2011/0187930 A1 | 8/2011 | Crabtree |
| 2011/0187931 A1 | 8/2011 | Kim |
| 2011/0202956 A1 | 8/2011 | Connelly et al. |
| 2011/0270549 A1 | 11/2011 | Jeansonne et al. |
| 2011/0282837 A1 | 11/2011 | Gounares et al. |
| 2011/0283311 A1 | 11/2011 | Luong |
| 2011/0295396 A1 | 12/2011 | Chinen et al. |
| 2012/0019388 A1 | 1/2012 | Kates |
| 2012/0047532 A1 | 2/2012 | McCarthy |
| 2012/0059495 A1 | 3/2012 | Weiss et al. |
| 2012/0069246 A1 | 3/2012 | Thornberry et al. |
| 2012/0094696 A1 | 4/2012 | Ahn et al. |
| 2012/0124456 A1 | 5/2012 | Perez et al. |
| 2012/0271670 A1 | 10/2012 | Zaloom |
| 2012/0280802 A1 | 11/2012 | Yoshida et al. |
| 2012/0291068 A1 | 11/2012 | Khushoo et al. |
| 2012/0326835 A1 | 12/2012 | Cockrell et al. |
| 2013/0046800 A1 | 2/2013 | Assi et al. |
| 2013/0053063 A1 | 2/2013 | McSheffrey |
| 2013/0060358 A1 | 3/2013 | Li et al. |
| 2013/0070044 A1 | 3/2013 | Naidoo et al. |
| 2013/0074061 A1 | 3/2013 | Averbuch et al. |
| 2013/0090213 A1 * | 4/2013 | Amini ................. G06F 19/3481 482/8 |
| 2013/0138757 A1 | 5/2013 | Ferron |
| 2013/0152139 A1 | 6/2013 | Davis et al. |
| 2013/0204408 A1 | 8/2013 | Thiruvengada et al. |
| 2013/0267383 A1 * | 10/2013 | Watterson .......... A63B 22/0235 482/4 |
| 2013/0300576 A1 | 11/2013 | Sinsuan et al. |
| 2013/0318559 A1 | 11/2013 | Crabtree |
| 2013/0321637 A1 | 12/2013 | Frank et al. |
| 2013/0324247 A1 | 12/2013 | Esaki et al. |
| 2014/0101465 A1 | 4/2014 | Wang et al. |

(56) References Cited

U.S. PATENT DOCUMENTS

| | | |
|---|---|---|
| 2014/0168277 A1 | 6/2014 | Ashley et al. |
| 2014/0192197 A1 | 7/2014 | Hanko et al. |
| 2014/0218517 A1 | 8/2014 | Kim et al. |
| 2014/0266669 A1 | 9/2014 | Fadell et al. |
| 2014/0266684 A1 | 9/2014 | Poder et al. |
| 2014/0310075 A1 | 10/2014 | Ricci |
| 2014/0351832 A1 | 11/2014 | Cho et al. |
| 2014/0373074 A1 | 12/2014 | Hwang et al. |
| 2015/0054910 A1 | 2/2015 | Offen et al. |
| 2015/0106866 A1 | 4/2015 | Fujita |
| 2015/0143408 A1 | 5/2015 | Sallas |
| 2015/0156612 A1 | 6/2015 | Vemulapalli |
| 2015/0159401 A1 | 6/2015 | Patrick et al. |
| 2015/0160623 A1 | 6/2015 | Holley |
| 2015/0160634 A1 | 6/2015 | Smith et al. |
| 2015/0160635 A1 | 6/2015 | Schofield et al. |
| 2015/0160636 A1 | 6/2015 | McCarthy et al. |
| 2015/0160663 A1 | 6/2015 | McCarthy et al. |
| 2015/0161452 A1 | 6/2015 | McCarthy et al. |
| 2015/0161882 A1 | 6/2015 | Lett |
| 2015/0162006 A1 | 6/2015 | Kummer |
| 2015/0163411 A1 | 6/2015 | McCarthy et al. |
| 2015/0163412 A1 | 6/2015 | Holley et al. |
| 2015/0163535 A1 | 6/2015 | McCarthy et al. |
| 2015/0172742 A1 | 6/2015 | Richardson |
| 2015/0309487 A1 | 10/2015 | Lyman |
| 2016/0063854 A1 | 3/2016 | Burton et al. |
| 2016/0066046 A1 | 3/2016 | Mountain |
| 2016/0091471 A1 | 3/2016 | Benn |
| 2016/0109864 A1 | 4/2016 | Lonn |
| 2016/0182249 A1 | 6/2016 | Lea |
| 2016/0191912 A1 | 6/2016 | Lea et al. |
| 2016/0191990 A1 | 6/2016 | McCarthy |
| 2016/0203700 A1 | 7/2016 | Bruhn et al. |

FOREIGN PATENT DOCUMENTS

| | | |
|---|---|---|
| GB | 2 304 952 A | 3/1997 |
| JP | 2008148016 A | 6/2008 |
| WO | 93/20544 A1 | 10/1993 |
| WO | 2004/068386 A1 | 8/2004 |
| WO | 2011/095567 A1 | 8/2011 |
| WO | 2016/034880 A1 | 3/2016 |

OTHER PUBLICATIONS

"Do you want to know how to find water leaks? Use a Bravedo Water Alert Flow Monitor to find out!", Bravedo.com, accessed Dec. 16, 2014, 10 pages. Retrieved from http://bravedo.com/.

"Flow Pulse®, Non-invasive clamp-on flow monitor for pipes," Pulsar Process Measurement Ltd, accessed on Dec. 16, 2014, 2 pages. Retrieved from http://www.pulsar-pm.com/product-types/flow/flow-pulse.aspx.

"Introduction to Ultrasonic Doppler Flowmeters," OMEGA Engineering inc., accessed on Dec. 16, 2014, 3 ppages. Retrieved from http://www.omega.com/prodinfo/ultrasonicflowmeters.html.

"Ultrasonic Flow Meters," RS Hydro Ltd, accessed on Dec. 16, 2014, 3 pages. Retrieved from http://www.rshydro.co.uk/ultrasonic-flowmeter.shtml.

Wang et al., "Mixed Sound Event Verification on Wireless Sensor Network for Home Automation," IEEE Transactions on Industrial Informatics, vol. 10, No. 1, Feb. 2014, 10 pages.

International Search Report and Written Opinion for PCT/US2014/055441 mailed Dec. 4, 2014, 10 pages.

International Search Report and Written Opinion for PCT/US2014/055476 mailed Dec. 30, 2014, 10 pages.

Mexican Institute of Industrial Property Office Action dated Nov. 1, 2013, for Mex. Patent Appln No. MX/a/2012/008882 is not translated into English, 3 pages.

Mexican Institute of Industrial Property Notice of Allowance dated Feb. 10, 2014, for Mex. Patent Appln No. MX/a/2012/008882, 1 page.

U.S. Appl. No. 12/700,310, filed Feb. 4, 2010 Non-Final Office Action mailed Mar. 11, 2015, 35 pages.

U.S. Appl. No. 14/107,132, filed Dec. 16, 2013, Non Final Office Action mailed May 27, 2015, 26 pages.

U.S. Appl. No. 14/485,188, filed Sep. 12, 2014, Pre-Interview First Office Action mailed Jul. 29, 2015, 20 pages.

U.S. Appl. No. 14/485,188, filed Sep. 12, 2014, Pre-Interview First Office Action mailed Oct. 1, 2015, 10 pages.

Author Unknown, "AllJoyn Onboarding Service Frameworks," Qualcomm Connected Experiences, Inc., ac cessed on Jul. 15, 2014, 9 pages. Retrieved from https://www.alljoyn.org.

Author Unknown, "App for Samsung Smart TV®," Crestron Electronics, Inc., accessed on Jul. 14, 2014, 3 pages. Retrieved from http://www.crestron.com/products/smart tv television apps/.

Author Unknown, "International Building Code Excerpts, Updated with recent code changes that impact electromagnetic locks," Securitron, Assa Abloy, 2007, 2009,2 pages.Retrieved from: www.securitron.com/Other/.../New_IBC-IFC_Code_Language.pdf.

Author Unknown, "Voice Activated TV using the Amulet Remote for Media Center," AmuletDevices.com, accessed on Jul. 14, 2014, 1 page. Retrieved from http://www.amuletdevices.com/index.php/Features/television.html.

International Search Report and Written Opinion of PCT/EP2011/051608 mailed on May 30, 2011, 11 pages.

International Preliminary Report on Patentability for PCT/EP2011/051608 mailed Aug. 16, 2012, 8 pages.

International Search Report and Written Opinion of PCT/US2014/053876 mailed Nov. 26, 2014, 9 pages.

Lamonica, M., "CES 2010 Preview: Green comes in many colors," retrieved from CNET.com (http://ces.cnet.com/8301-31045_1-10420381-269.html), Dec. 22, 2009, 2 pages.

Mexican Institute of Industrial Property Office Action dated Dec. 16, 2013, for Mex. Patent Appin No. MX/a/2012/008882, 3 pages.

Robbins, Gordon, Deputy Chief, "Addison Fire Department Access Control Installation," 2006 International Fire Code, Section 1008.1.3.4, 4 pages.

U.S. Appl. No. 12/700,310, filed Feb. 4, 2010 Non-Final Office Action mailed Aug. 14, 2014, 18 pages.

U.S. Appl. No. 12/700,310, filed Feb. 4, 2010 Final Office Action mailed Feb. 28, 2014, 17 pages.

U.S. Appl. No. 12/700,310, filed Feb. 4, 2010 Non-Final Office Action mailed Oct. 15, 2013, 15 pages.

U.S. Appl. No. 12/700,310, filed Feb. 4, 2010 Non-Final Office Action mailed Apr. 1, 2013, 16 pages.

U.S. Appl. No. 12/700,310, filed Feb. 4, 2010, Final Office Action mailed Oct. 10, 2012, 16 pages.

U.S. Appl. No. 12/700,310, filed Feb. 4, 2010, Office Action mailed May 4, 2012, 15 pages.

U.S. Appl. No. 12/700,408, filed Feb. 4, 2010, Notice of Allowance mailed Jul. 28, 2012, 8 pages.

U.S. Appl. No. 13/680,934, filed Nov. 19, 2012, Notice of Allowance mailed Jul. 25, 2014, 12 pages.

U.S. Appl. No. 13/680,934, filed Nov. 19, 2012, Notice of Allowance mailed Apr. 30, 2014, 9 pages.

U.S. Appl. No. 13/680,934, filed Nov. 19, 2012, Final Office Action mailed Feb. 10, 2014, 13 pages.

U.S. Appl. No. 13/680,934, filed Nov. 19, 2012, Non-Final Office Action mailed Oct. 2, 2013, 7 pages.

Fong A.C.M. et al, "Indoor air quality control for asthma patients using smart home technology," Consumer Electronics (ISCE), 2011 IEEE 15th International Symposium on, IEEE, Jun. 14, 2011, pp. 18-19, XP032007803, DOI: 10.1109/ISCE.2011.5973774, ISBN: 978-1-61284-843-3, Abstract and sections 3 and 4.

Shunfeng Cheng et al., "A Wireless Sensor System for Prognostics and Health Management," IEEE Sensors Journal, IEEE Service Center, New York, NY, US, vol. 10, No. 4, Apr. 1, 2010, pp. 856-862, XP011304455, ISSN: 1530-437X, Sections 2 and 3.

International Search Report and Written Opinion for PCT/EP2015/070286 mailed Nov. 5, 2015, 13 pages.

International Search Report and Written Opinion for PCT/GB2015/052544 mailed Nov. 6, 2015, 10 pages.

U.S. Appl. No. 14/470,352, filed Aug. 27, 2014 Non Final Office Action mailed Nov. 20, 2015, 28 pages.

(56) References Cited

OTHER PUBLICATIONS

International Search Report and Written Opinion for PCT/GB2015/052457 mailed Nov. 13, 2015, 11 pages.
U.S. Appl. No. 12/700,310 filed Feb. 4, 2010 Final Office Action mailed Oct. 26, 2015, 19 pages.
U.S. Appl. No. 14/107,132 filed Dec. 16, 2013, Final Rejection mailed Dec. 16, 2015, 32 pages.
International Search Report and Written Opinion for PCT/EP2015/073299 mailed Jan. 4, 2016, 12 pages.
International Search Report and Written Opinion for PCT/EP2015/073936 mailed Feb. 4, 2016, all pages.
U.S. Appl. No. 14/485,188, filed Sep. 12, 2014, Final Rejection mailed Feb. 23, 2016, 22 pages.
U.S. Appl. No. 14/567,348, filed Dec. 11, 2014, Preinterview first office action mailed Jan. 20, 2016, 23 pages.
U.S. Appl. No. 14/470,352 filed Aug. 27, 2014 Final Office Action mailed Mar. 17, 2016, all pages.
U.S. Appl. No. 14/567,765, filed Dec. 11, 2014, Preinterview first office action mailed Apr. 8, 2016, 30 pages.
U.S. Appl. No. 14/577,717, filed Dec. 19, 2014, Preinterview first office action mailed Apr. 4, 2016, 29 pages.
U.S. Appl. No. 14/584,075, filed Dec. 29, 2014, Non-Final Rejection mailed Apr. 1, 2016, 40 pages.
International Search Report and Written Opinion for PCT/US2016/028126 mailed Jun. 3, 2016, all pages.
U.S. Appl. No. 12/700,310, filed Feb. 4, 2010 Non-Final Office Action mailed Jun. 16, 2016, 30 pages.
U.S. Appl. No. 12/485,188, filed Sep. 12, 2014 Non-Final Rejection mailed Jun. 17, 2016, 29 pages.
U.S. Appl. No. 14/710,331, filed May 12, 2015 Non-Final Rejection mailed May 20, 2016, 42 pages.
U.S. Appl. No. 14/470,352, filed Aug. 27, 2014 Non-Final Office Action mailed Aug. 26, 2016, all pages.
U.S. Appl. No. 14/107,132, filed Dec. 16, 2013 Non-Final Office Action mailed Jul. 26, 2016, all pages.
U.S. Appl. No. 14/715,248, filed May 18, 2015 Non-Final Rejection mailed Jul. 19, 2016, 34 pages.
U.S. Appl. No. 14/567,783, filed Dec. 11, 2014 Non-Final Rejection mailed Aug. 23, 2016, all pages.

* cited by examiner

FITNESS OVERLAY AND INCORPORATION FOR HOME AUTOMATION SYSTEM

TECHNICAL FIELD

The present technology relates to systems and methods for incorporating and displaying content. More specifically, the present technology relates to fitness content incorporated into a home automation system.

BACKGROUND

People interested in physical fitness have a variety of options available. From going to the gym to buying equipment for the home, many options provide people of all skill levels with the ability to invest in their fitness. However, many options available can be quite expensive if a user is interested in monitoring physical attributes while exercising. While attending a gym can provide access to high-tech equipment, membership fees can be prohibitive. Similarly, while a person can purchase a technically advanced piece of equipment, this may also prove expensive for an individual interested in getting fit without spending too much money. Although other avenues are available, budget equipment may not provide the accessibility or information that a user desires.

Thus, there is a need for improved methods and systems for providing and displaying fitness content. These and other needs are addressed by the present technology.

SUMMARY

Systems and methods for displaying fitness information with an electronic device may include receiving multimedia content at an input of the electronic device. The electronic device may provide the audiovisual content to a display device. The electronic device may also receive fitness information, and may provide this fitness information to the display device.

The fitness information may be received from an exercise device, and may also be received from a mobile device. The fitness information may be received from a remote control associated with the electronic device, and the remote control may be communicatively coupled with the exercise device. The fitness information presented may be unrelated to the audiovisual or multimedia content in disclosed embodiments. The methods may further include receiving input at the electronic device from a remote control associated with the electronic device, and providing a control signal from the electronic device to an exercise device to adjust operation of the exercise equipment device commensurate with the received input. The fitness information may include one or more items of vital information about the user, or one or more items of operational information about the exercise device.

The fitness information may be provided to the display device overlaying the audiovisual or multimedia content provided to the display device. The fitness information may be provided automatically, or may be provided in response to a control signal received from a remote control associated with the electronic device, where the fitness information may be provided in a dedicated portion of the display device. The methods may further include receiving an input from a remote control associated with the electronic device to scroll to additional fitness information being received by the electronic device. The method may still further include receiving temperature information at the electronic device from a temperature sensor, determining at the electronic device that the temperature of the space has increased since the fitness information reception began, and providing a control signal from the electronic device to a communicatively coupled heating or air conditioning system to adjust the temperature of the space.

The present technology also includes electronic devices for use in home automation systems. The devices may include a first input component configured to receive multimedia data, a second input component configured to receive fitness information, and at least one output component communicatively coupled with at least one display device. The electronic devices may include one or more processors, and memory communicatively coupled with and readable by the one or more processors and having stored therein processor-readable instructions, which when executed by the one or more processors cause the one or more processors to perform functions. The functions performed may include receiving multimedia content through the first input component, and providing the multimedia content through the at least one output. The functions may also include receiving fitness information through the second input component, and providing the fitness information through the at least one output component.

The fitness information may be received from a communicatively coupled exercise device, and may be received from a communicatively coupled mobile device configured to acquire the fitness information. The electronic device may include a television receiver, and the device may further include a remote control communicatively coupled with both the electronic device and an exercise device. The processors may be further caused to combine the received fitness information with the multimedia content as a single output. The processors may be still further caused to receive temperature information from one or more communicatively coupled temperature sensors. The processors may be caused to determine, based on the received temperature information, that the temperature of a space associated with the electronic device has changed, and also to provide a control signal to a heating or air conditioning device to adjust the temperature of the space.

Such technology may provide numerous benefits over conventional techniques. For example, the technology may allow enabled devices to provide the fitness information as an overlay on a display device showing additional content. Additionally, the technology may allow more generic exercise equipment to be used with a mobile device. The mobile device may be configured to collect the fitness information and provide it for display while a user is watching additional content. These and other embodiments, along with many of their advantages and features, are described in more detail in conjunction with the below description and attached figures.

BRIEF DESCRIPTION OF THE DRAWINGS

A further understanding of the nature and advantages of the disclosed embodiments may be realized by reference to the remaining portions of the specification and the drawings.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

A television receiver may serve as a host for a home automation system. By using a television receiver to host a home automation system, various advantages may be realized. For instance, the home automation system may be able to conveniently present home automation information to a user via a connected display device, such as a television or other connected devices, such as a tablet computer, mobile phone, monitor, or laptop computer. In an exemplary operation, the home automation system may be utilized with exercise equipment to collect fitness information that may be presented on a connected display device. As will be explained below, the technology allows a variety of devices to be interconnected or utilized to allow a user to see fitness information on the display device while they are otherwise watching additional or alternative content. After describing media service systems and electronic devices in FIGS. 1 and 2 that may be utilized in the present technology, methods and systems will be explained with the remaining figures.

Figure 1:
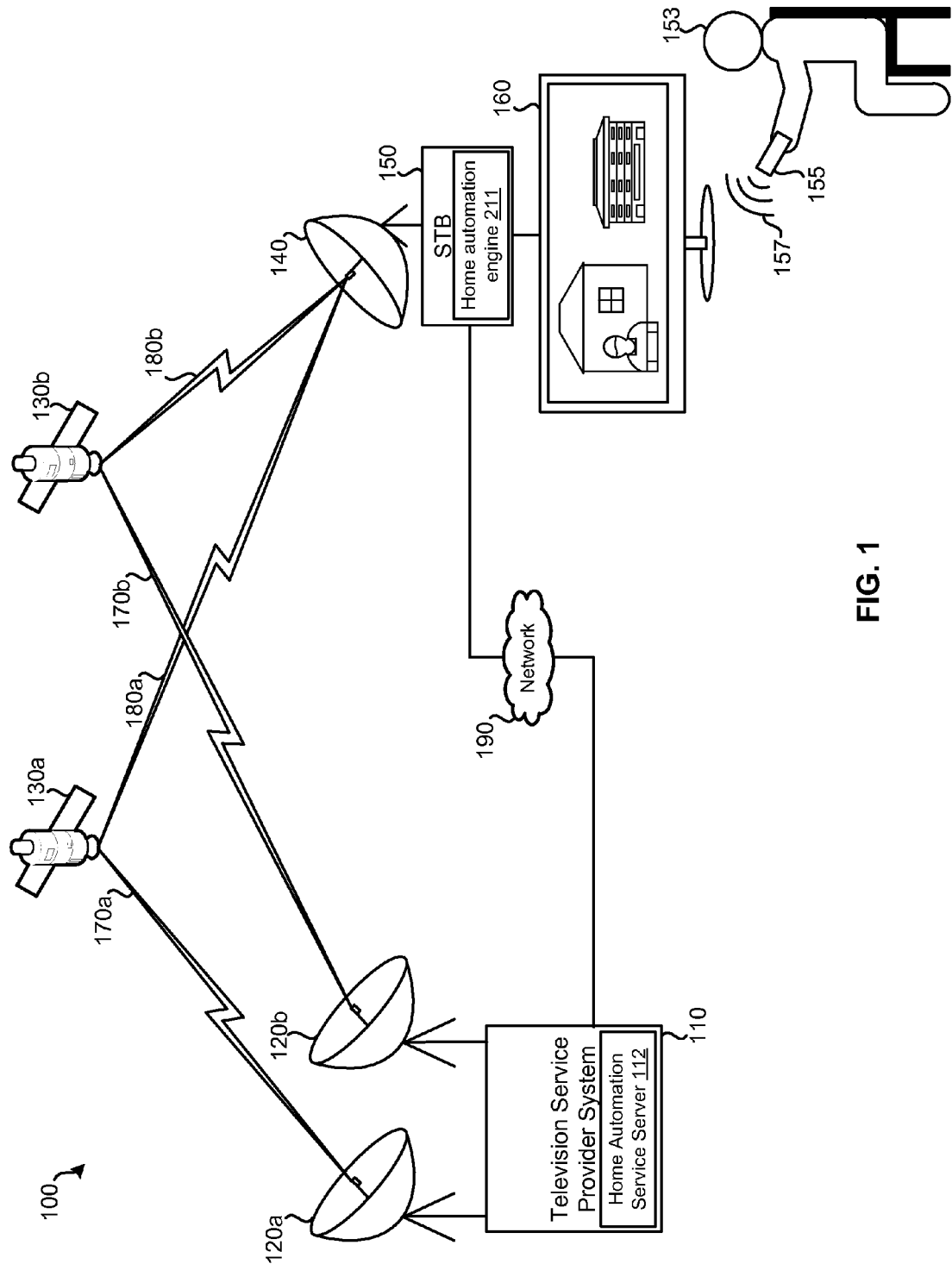
FIG. 1 shows a simplified media service system that may be used in accordance with embodiments of the present technology.

FIG. 1 illustrates an embodiment of a satellite television distribution system 100. While a home automation system may be incorporated with various types of television receivers, various embodiments may be part of a satellite-based television distribution system. Cable, IP-based, wireless, and broadcast focused systems are also possible. Satellite television distribution system 100 may include: television service provider system 110, satellite transmitter equipment 120, satellites 130, satellite dish 140, television receiver 150, home automation service server 112, and display device 160. The display device 160 can be controlled by a user 153 using a remote control device 155 that can send wired or wireless signals 157 to communicate with the STB 150 and/or display device 160. Alternate embodiments of satellite television distribution system 100 may include fewer or greater numbers of components. While only one satellite dish 140, television receiver 150, and display device 160 (collectively referred to as "user equipment") are illustrated, it should be understood that multiple (e.g., tens, thousands, millions of) instances and types of user equipment may receive data and television signals from television service provider system 110 via satellites 130.

Television service provider system 110 and satellite transmitter equipment 120 may be operated by a television service provider. A television service provider may distribute television channels, on-demand programming, programming information, and/or other content/services to users. Television service provider system 110 may receive feeds of one or more television channels and content from various sources. Such television channels may include multiple television channels that contain at least some of the same content (e.g., network affiliates). To distribute television channels for presentation to users, feeds of the television channels may be relayed to user equipment via multiple television distribution satellites. Each satellite may relay multiple transponder streams. Satellite transmitter equipment 120 may be used to transmit a feed of one or more television channels from television service provider system 110 to one or more satellites 130. While a single television service provider system 110 and satellite transmitter equipment 120 are illustrated as part of satellite television distribution system 100, it should be understood that multiple instances of transmitter equipment may be used, possibly scattered geographically, to communicate with satellites 130. Such multiple instances of satellite transmitting equipment may communicate with the same or with different satellites. Different television channels may be transmitted to satellites 130 from different instances of transmitting equipment. For instance, a different satellite dish of satellite transmitter equipment 120 may be used for communication with satellites in different orbital slots.

Satellites 130 may be configured to receive signals, such as streams of television channels, from one or more satellite uplinks such as satellite transmitter equipment 120. Satellites 130 may relay received signals from satellite transmitter equipment 120 (and/or other satellite transmitter equipment) to multiple instances of user equipment via transponder streams. Different frequencies may be used for uplink signals 170 from downlink signals 180. Satellites 130 may be in geosynchronous orbit. Each of the transponder streams transmitted by satellites 130 may contain multiple television channels transmitted as packetized data. For example, a single transponder stream may be a serial digital packet stream containing multiple television channels. Therefore, packets for multiple television channels may be interspersed. Further, information used by television receiver 150 for home automation functions may also be relayed to a television receiver via one or more transponder streams.

Multiple satellites 130 may be used to relay television channels from television service provider system 110 to satellite dish 140. Different television channels may be carried using different satellites. Different television channels may also be carried using different transponders of the same satellite; thus, such television channels may be transmitted at different frequencies and/or different frequency ranges. As an example, a first and second television channel may be relayed via a first transponder of satellite 130a. A third, fourth, and fifth television channel may be relayed via a different satellite or a different transponder of the same satellite relaying the transponder stream at a different frequency. A transponder stream transmitted by a particular transponder of a particular satellite may include a finite number of television channels, such as seven. Accordingly, if many television channels are to be made available for viewing and recording, multiple transponder streams may be necessary to transmit all of the television channels to the instances of user equipment.

Satellite dish 140 may be a piece of user equipment that is used to receive transponder streams from one or more satellites, such as satellites 130. Satellite dish 140 may be provided to a subscriber for use on a subscription basis to receive television channels provided by the television service provider system 110, satellite transmitter equipment 120, and/or satellites 130. Satellite dish 140, which may include one or more low noise blocks (LNBs), may be configured to receive transponder streams from multiple satellites and/or multiple transponders of the same satellite. Satellite dish 140 may be configured to receive television channels via transponder streams on multiple frequencies. Based on the characteristics of television receiver 150 and/or satellite dish 140, it may only be possible to capture transponder streams from a limited number of transponders concurrently. For example, a tuner of television receiver 150 may only be able to tune to a single transponder stream from a transponder of a single satellite at a given time. The tuner can then be re-tuned to another transponder of the same or a different satellite. A television receiver 150 having multiple tuners may allow for multiple transponder streams to be received at the same time.

Figure 2:
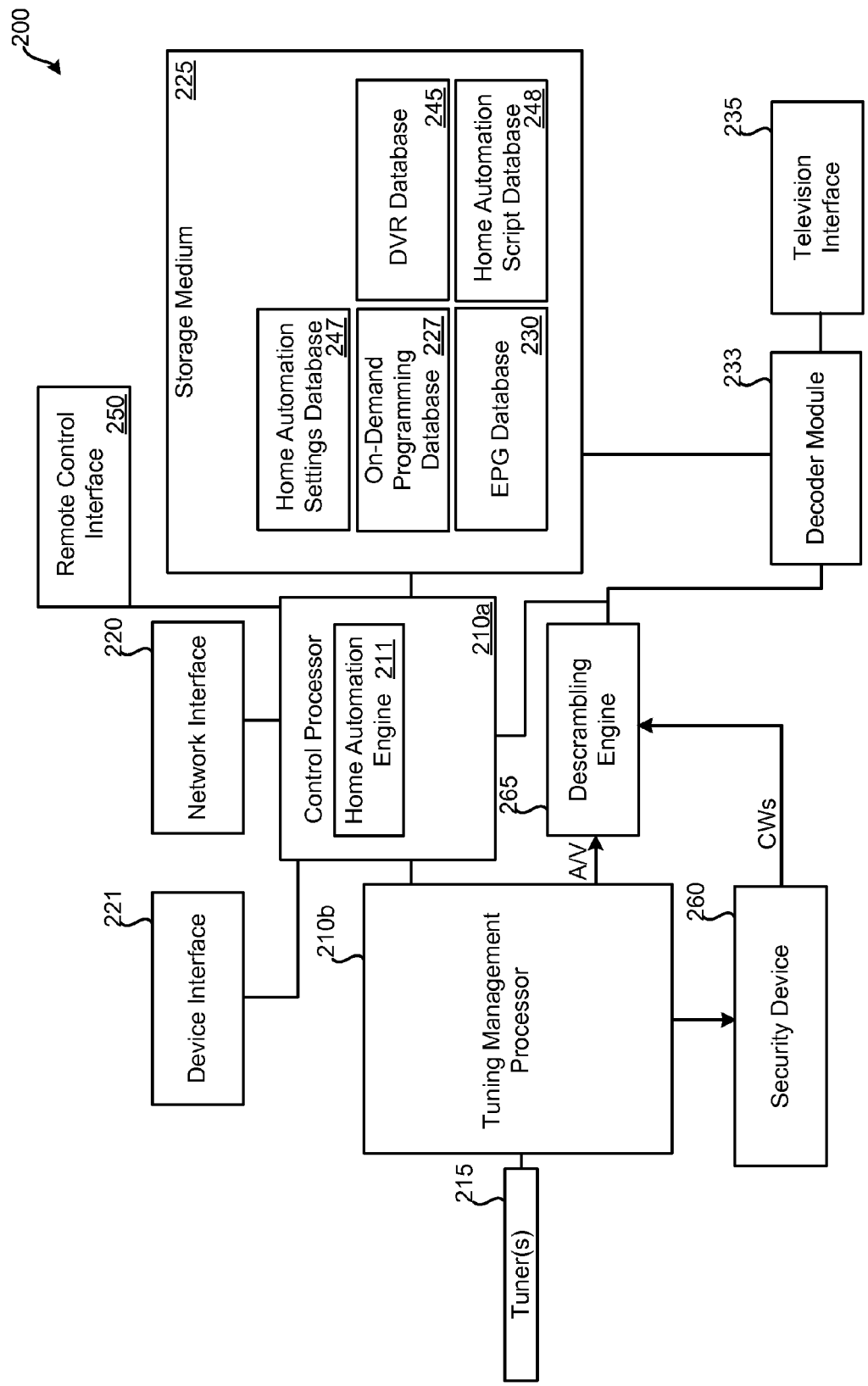
FIG. 2 illustrates an exemplary electronic device that may be used in accordance with embodiments of the present technology.

In communication with satellite dish 140 may be one or more television receivers. Television receivers may be configured to decode signals received from satellites 130 via satellite dish 140 for output and presentation via a display device, such as display device 160. A television receiver may be incorporated as part of a television or may be part of a separate device, commonly referred to as a set-top box (STB). Television receiver 150 may decode signals received via satellite dish 140 and provide an output to display device 160. On-demand content, such as PPV content, may be stored to a computer-readable storage medium. FIG. 2 provides additional detail of various embodiments of a television receiver. A television receiver is defined to include set-top boxes (STBs), and also circuitry having similar functionality that may be incorporated with another device. For instance, circuitry similar to that of a television receiver may be incorporated as part of a television. As such, while FIG. 1 illustrates an embodiment of television receiver 150 as separate from display device 160, it should be understood that, in other embodiments, similar functions may be performed by a television receiver integrated with display device 160. Television receiver 150 may include home automation engine 211, as detailed in relation to FIG. 2.

Display device 160 may be used to present video and/or audio decoded and output by television receiver 150. Television receiver 150 may also output a display of one or more interfaces to display device 160, such as an electronic programming guide (EPG). In many embodiments, display device 160 is a television. Display device 160 may also be a monitor, computer, or some other device configured to display video and, possibly, play audio.

Uplink signal 170a represents a signal between satellite transmitter equipment 120 and satellite 130a. Uplink signal 170b represents a signal between satellite transmitter equipment 120 and satellite 130b. Each of uplink signals 170 may contain streams of one or more different television channels. For example, uplink signal 170a may contain a first group of television channels, while uplink signal 170b contains a second group of television channels. Each of these television channels may be scrambled such that unauthorized persons are prevented from accessing the television channels.

Downlink signal 180a represents a signal between satellite 130a and satellite dish 140. Downlink signal 180b represents a signal between satellite 130b and satellite dish 140. Each of downlink signals 180 may contain one or more different television channels, which may be at least partially scrambled. A downlink signal may be in the form of a transponder stream. A single transponder stream may be tuned to at a given time by a tuner of a television receiver. For example, downlink signal 180a may be a first transponder stream containing a first group of television channels, while downlink signal 180b may be a second transponder stream containing a different group of television channels. In addition to or instead of containing television channels, a transponder stream can be used to transmit on-demand content to television receivers, including PPV content, which may be stored locally by the television receiver until output for presentation.

FIG. 1 illustrates downlink signal 180a and downlink signal 180b, being received by satellite dish 140 and distributed to television receiver 150. For a first group of television channels, satellite dish 140 may receive downlink signal 180a and for a second group of channels, downlink signal 180b may be received. Television receiver 150 may decode the received transponder streams. As such, depending on which television channels are desired to be presented or stored, various transponder streams from various satellites may be received, descrambled, and decoded by television receiver 150.

Network 190, which may include the Internet, may allow for bidirectional communication between television receiver 150 and television service provider system 110, such as for home automation related services provided by home automation service server 112. In addition or in alternate to network 190, a telephone, e.g., landline, or cellular connection may be used to enable communication between television receiver 150 and television service provider system 110.

FIG. 2 illustrates an embodiment of a television receiver 200, which may represent television receiver 150 of FIG. 1. Television receiver 200 may be configured to function as a host for a home automation system either alone or in conjunction with a communication device. Television receiver 200 may be in the form of a separate device configured to be connected with a display device, such as a television. Embodiments of television receiver 200 can include set top boxes (STBs). In addition to being in the form of an STB, a television receiver may be incorporated as part of another device, such as a television, other form of display device, video game console, computer, mobile phone or tablet, or the like. For example, a television may have an integrated television receiver, which does not involve an external STB being coupled with the television.

Television receiver 200 may be incorporated as part of a television, such as display device 160 of FIG. 1. Television receiver 200 may include: processors 210, which may include control processor 210a, tuning management processor 210b, and possibly additional processors, tuners 215, network interface 220, non-transitory computer-readable storage medium 225, electronic programming guide (EPG) database 230, television interface 235, digital video recorder (DVR) database 245, which may include provider-managed television programming storage and/or user-defined television programming, on-demand programming database 227, home automation settings database 247, home automation script database 248, remote control interface 250, security device 260, and/or descrambling engine 265. In other embodiments of television receiver 200, fewer or greater numbers of components may be present. It should be understood that the various components of television receiver 200 may be implemented using hardware, firmware, software, and/or some combination thereof. Functionality of components may be combined; for example, functions of descrambling engine 265 may be performed by tuning management processor 210b. Further, functionality of components may be spread among additional components.

Processors 210 may include one or more specialized and/or general-purpose processors configured to perform processes such as tuning to a particular channel, accessing and displaying EPG information from EPG database 230, and/or receiving and processing input from a user. It should be understood that the functions performed by various modules of FIG. 2 may be performed using one or more processors. As such, for example, functions of descrambling engine 265 may be performed by control processor 210a.

Control processor 210a may communicate with tuning management processor 210b. Control processor 210a may control the recording of television channels based on timers stored in DVR database 245. Control processor 210a may also provide commands to tuning management processor 210b when recording of a television channel is to cease. In addition to providing commands relating to the recording of television channels, control processor 210a may provide commands to tuning management processor 210b that indicate television channels to be output to decoder module 233 for output to a display device. Control processor 210a may also communicate with network interface 220 and remote control interface 250. Control processor 210a may handle incoming data from network interface 220 and remote control interface 250. Additionally, control processor 210a may be configured to output data via network interface 220.

Control processor 210a may include home automation engine 211. Home automation engine 211 may permit television receiver and control processor 210a to provide home automation functionality. Home automation engine 211 may have a JSON (JavaScript Object Notation) command interpreter or some other form of command interpreter that is configured to communicate with wireless devices via network interface 220 and a message server, possibly via a message server client. Such a command interpreter of home automation engine 211 may also communicate via a local area network with devices without using the Internet. Home automation engine 211 may contain multiple controllers specific to different protocols; for instance, a ZigBee® controller, a Z-Wave® controller, and/or an IP camera controller, wireless LAN, 802.11, may be present. Home automation engine 211 may contain a media server configured to serve streaming audio and/or video to remote devices on a local area network or the Internet. Television receiver may be able to serve such devices with recorded content, live content, and/or content recorded using one or more home automation devices, such as cameras.

Tuners 215 may include one or more tuners used to tune to transponders that include broadcasts of one or more television channels. Such tuners may be used also to receive for storage on-demand content and/or addressable television commercials. In some embodiments, two, three, or more than three tuners may be present, such as four, six, or eight tuners. Each tuner contained in tuners 215 may be capable of receiving and processing a single transponder stream from a satellite transponder or from a cable network at a given time. As such, a single tuner may tune to a single transponder stream at a given time. If tuners 215 include multiple tuners, one tuner may be used to tune to a television channel on a first transponder stream for display using a television, while another tuner may be used to tune to a television channel on a second transponder for recording and viewing at some other time. If multiple television channels transmitted on the same transponder stream are desired, a single tuner of tuners 215 may be used to receive the signal containing the multiple television channels for presentation and/or recording. Tuners 215 may receive commands from tuning management processor 210b. Such commands may instruct tuners 215 to which frequencies are to be tuned.

Network interface 220 may be used to communicate via an alternate communication channel with a television service provider, if such communication channel is available. A communication channel may be via satellite, which may be unidirectional to television receiver 200, and the alternate communication channel, which may be bidirectional, may be via a network, such as the Internet. Data may be transmitted from television receiver 200 to a television service provider system and from the television service provider system to television receiver 200. Information may be transmitted and/or received via network interface 220. For instance, instructions from a television service provider may also be received via network interface 220, if connected with the Internet. Besides the primary communication channel being satellite, cable network, an IP-based network, or broadcast network may be used. Network interface 220 may permit wireless communication with one or more types of networks, including using home automation network protocols and wireless network protocols. Also, wired networks may be connected to and communicated with via network interface 220. Device interface 221 may represent a USB port or some other form of communication port that permits communication with a communication device or an enabled exercise device as will be explained further below.

Storage medium 225 may represent one or more non-transitory computer-readable storage mediums. Storage medium 225 may include memory and/or a hard drive. Storage medium 225 may be used to store information received from one or more satellites and/or information received via network interface 220. Storage medium 225 may store information related to on-demand programming database 227, EPG database 230, DVR database 245, home automation settings database 247, and/or home automation script database 248. Recorded television programs may be stored using storage medium 225 as part of DVR database 245. Storage medium 225 may be partitioned or otherwise divided, such as into folders, such that predefined amounts of storage medium 225 are devoted to storage of television programs recorded due to user-defined timers and stored television programs recorded due to provider-defined timers.

Home automation settings database 247 may allow configuration settings of home automation devices and user preferences to be stored. Home automation settings database 247 may store data related to various devices that have been set up to communicate with television receiver 200. For instance, home automation settings database 247 may be configured to store information on which types of events should be indicated to users, to which users, in what order, and what communication methods should be used. For instance, an event such as an open garage may only be notified to certain wireless devices, e.g., a cellular phone associated with a parent, not a child, notification may be by a third-party notification server, email, text message, and/or phone call. In some embodiments, a second notification method may only be used if a first fails. For instance, if a notification cannot be sent to the user via a third-party notification server, an email may be sent.

Home automation settings database 247 may store information that allows for the configuration and control of individual home automation devices which may operate using Z-wave and Zigbee-specific protocols. To do so, home automation engine 211 may create a proxy for each device that allows for settings for the device to be passed through a UI, e.g, presented on a television, to allow for settings to be solicited for and collected via a user interface presented by television receiver or overlay device. The received settings may then be handled by the proxy specific to the protocol, allowing for the settings to be passed on to the appropriate device. Such an arrangement may allow for settings to be collected and received via a UI of the television receiver or overlay device and passed to the appropriate home automation device and/or used for managing the appropriate home automation device. For example, an piece of exercise equipment that is enabled to interface with the home automation engine 211, such as via device interface 221, may be configured at the electronic device 211 in addition to on the piece of exercise equipment itself. Additionally, a mobile device or application residing on a mobile device and utilized with exercise equipment as will be explained below, may be configured in such a fashion as well for displaying received fitness information on a coupled display device.

Home automation script database 248 may store scripts that detail how home automation devices are to function based on various events occurring. For instance, if stored content starts being played back by television receiver 200, lights in the vicinity of display device 160 may be dimmed and shades may be lowered by communicatively coupled and controlled shade controller. As another example, when a user shuts programming off late in the evening, there may be an assumption the user is going to bed. Therefore, the user may configure television receiver 200 to lock all doors via a lock controller, shut the garage door via garage controller, lower a heat setting of thermostat, shut off all lights via a light controller, and determine if any windows or doors are open via window sensors and door sensors, and, if so, alert the user. Such scripts or programs may be predefined by the home automation/television service provider and/or may be defined by a user.

In some embodiments, home automation script database 248 may allow for various music profiles to be implemented. For instance, based on home automation settings within a structure, appropriate music may be played. For instance, when an piece of exercise equipment is connected or is used, energizing music may be played. Conversely, based on the music being played, settings of home automation devices may be determined. If television programming, such as a movie, is output for playback by television receiver 150, a particular home automation script may be used to adjust home automation settings, e.g., lower lights, raise temperature, and lock doors.

EPG database 230 may store information related to television channels and the timing of programs appearing on such television channels. EPG database 230 may be stored using storage medium 225, which may be a hard drive or solid-state drive. Information from EPG database 230 may be used to inform users of what television channels or programs are popular and/or provide recommendations to the user. Information from EPG database 230 may provide the user with a visual interface displayed by a television that allows a user to browse and select television channels and/or television programs for viewing and/or recording. Information used to populate EPG database 230 may be received via network interface 220, via satellite, or some other communication link with a television service provider, e.g., a cable network. Updates to EPG database 230 may be received periodically. EPG database 230 may serve as an interface for a user to control DVR functions of television receiver 200, and/or to enable viewing and/or recording of multiple television channels simultaneously. EPG database 240 may also contain information about on-demand content or any other form of accessible content.

Decoder module 233 may serve to convert encoded video and audio into a format suitable for output to a display device. For instance, decoder module 233 may receive MPEG video and audio from storage medium 225 or descrambling engine 265 to be output to a television. MPEG video and audio from storage medium 225 may have been recorded to DVR database 245 as part of a previously-recorded television program. Decoder module 233 may convert the MPEG video and audio into a format appropriate to be displayed by a television or other form of display device and audio into a format appropriate to be output from speakers, respectively. Decoder module 233 may have the ability to convert a finite number of television channel streams received from storage medium 225 or descrambling engine 265, simultaneously. For instance, decoders within decoder module 233 may be able to only decode a single television channel at a time. Decoder module 233 may have various numbers of decoders.

Television interface 235 may serve to output a signal to a television or another form of display device in a proper format for display of video and playback of audio. As such, television interface 235 may output one or more television channels, stored television programming from storage medium 225, e.g., television programs from DVR database 245, television programs from on-demand programming 230 and/or information from EPG database 230, to a television for presentation. Television interface 235 may also serve to output a CVM.

Digital Video Recorder (DVR) functionality may permit a television channel to be recorded for a period of time. DVR functionality of television receiver 200 may be managed by control processor 210a. Control processor 210a may coordinate the television channel, start time, and stop time of when recording of a television channel is to occur. DVR database 245 may store information related to the recording of television channels. DVR database 245 may store timers that are used by control processor 210a to determine when a television channel should be tuned to and its programs recorded to DVR database 245 of storage medium 225. In some embodiments, a limited amount of storage medium 225 may be devoted to DVR database 245. Timers may be set by the television service provider and/or one or more users of television receiver 200.

DVR database 245 may also be used to record recordings of service provider-defined television channels. For each day, an array of files may be created. For example, based on provider-defined timers, a file may be created for each recorded television channel for a day. For example, if four television channels are recorded from 6-10 PM on a given day, four files may be created; one for each television channel. Within each file, one or more television programs may be present. The service provider may define the television channels, the dates, and the time periods for which the television channels are recorded for the provider-defined timers. The provider-defined timers may be transmitted to television receiver 200 via the television provider's network. For example, in a satellite-based television service provider system, data necessary to create the provider-defined timers at television receiver 150 may be received via satellite.

On-demand programming database 227 may store additional television programming. On-demand programming database 227 may include television programming that was not recorded to storage medium 225 via a timer, either user- or provider-defined. Rather, on-demand programming may be programming provided to the television receiver directly for storage by the television receiver and for later presentation to one or more users. On-demand programming may not be user-selected. As such, the television programming stored to on-demand programming database 227 may be the same for each television receiver of a television service provider. On-demand programming database 227 may include pay-per-view (PPV) programming that a user must pay and/or use an amount of credits to view. For instance, on-demand programming database 227 may include movies that are not available for purchase or rental yet.

Referring back to tuners 215, television channels received via satellite or cable may contain at least some scrambled data. Packets of audio and video may be scrambled to prevent unauthorized users, e.g., nonsubscribers, from receiving television programming without paying the television service provider. When a tuner of tuners 215 is receiving data from a particular transponder of a satellite, the transponder stream may be a series of data packets corresponding to multiple television channels. Each data packet may contain a packet identifier (PID), which can be determined to be associated with a particular television channel. Particular data packets, referred to as entitlement control messages (ECMs), may be periodically transmitted. ECMs may be associated with another PID and may be encrypted; television receiver 200 may use decryption engine 261 of security device 260 to decrypt ECMs. Decryption of an ECM may only be possible if the user has authorization to access the particular television channel associated with the ECM. When an ECM is determined to correspond to a television channel being stored and/or displayed, the ECM may be provided to security device 260 for decryption.

When security device 260 receives an encrypted ECM, security device 260 may decrypt the ECM to obtain some number of control words. In some embodiments, from each ECM received by security device 260, two control words are obtained. In some embodiments, when security device 260 receives an ECM, it compares the ECM to the previously received ECM. If the two ECMs match, the second ECM is not decrypted because the same control words would be obtained. In other embodiments, each ECM received by security device 260 is decrypted; however, if a second ECM matches a first ECM, the outputted control words will match; thus, effectively, the second ECM does not affect the control words output by security device 260. Security device 260 may be permanently part of television receiver 200 or may be configured to be inserted and removed from television receiver 200, such as a smart card, cable card, or the like.

Tuning management processor 210*b* may be in communication with tuners 215 and control processor 210*a*. Tuning management processor 210*b* may be configured to receive commands from control processor 210*a*. Such commands may indicate when to start/stop receiving and/or recording of a television channel and/or when to start/stop causing a television channel to be output to a television. Tuning management processor 210*b* may control tuners 215. Tuning management processor 210*b* may provide commands to tuners 215 that instruct the tuners which satellite, transponder, and/or frequency to tune to. From tuners 215, tuning management processor 210*b* may receive transponder streams of packetized data.

Descrambling engine 265 may use the control words output by security device 260 in order to descramble video and/or audio corresponding to television channels for storage and/or presentation. Video and/or audio data contained in the transponder data stream received by tuners 215 may be scrambled. Video and/or audio data may be descrambled by descrambling engine 265 using a particular control word. Which control word output by security device 260 to be used for successful descrambling may be indicated by a scramble control identifier present within the data packet containing the scrambled video or audio. Descrambled video and/or audio may be output by descrambling engine 265 to storage medium 225 for storage, in DVR database 245, and/or to decoder module 233 for output to a television or other presentation equipment via television interface 235.

In some embodiments, the television receiver 200 may be configured to periodically reboot in order to install software updates downloaded over the network 190 or satellites 130. Such reboots may occur for example during the night when the users are likely asleep and not watching television. If the system utilizes a single processing module to provide television receiving and home automation functionality, then the security functions may be temporarily deactivated. In order to increase the security of the system, the television receiver 200 may be configured to reboot at random times during the night in order to allow for installation of updates. Thus, an intruder is less likely to guess the time when the system is rebooting. In some embodiments, the television receiver 200 may include multiple processing modules for providing different functionality, such as television receiving functionality and home automation, such that an update to one module does not necessitate reboot of the whole system. In other embodiments, multiple processing modules may be made available as a primary and a backup during any installation or update procedures.

For simplicity, television receiver 200 of FIG. 2 has been reduced to a block diagram; commonly known parts, such as a power supply, have been omitted. Further, some routing between the various modules of television receiver 200 has been illustrated. Such illustrations are for exemplary purposes only. The state of two modules not being directly or indirectly connected does not indicate the modules cannot communicate. Rather, connections between modules of the television receiver 200 are intended only to indicate possible common data routing. It should be understood that the modules of television receiver 200 may be combined into a fewer number of modules or divided into a greater number of modules. Further, the components of television receiver 200 may be part of another device, such as built into a television. Television receiver 200 may include one or more instances of various computerized components, such as disclosed in relation to computer system 600 of FIG. 6.

While the television receiver 200 has been illustrated as a satellite-based television receiver, it is to be appreciated that techniques below may be implemented in other types of television receiving devices, such a cable receivers, terrestrial receivers, IPTV receivers or the like. In some embodiments, the television receiver 200 may be configured as a hybrid receiving device, capable of receiving content from disparate communication networks, such as satellite and terrestrial television broadcasts. In some embodiments, the tuners may be in the form of network interfaces capable of receiving content from designated network locations. The home automation functions of television receiver 200 may be performed by an overlay device. If such an overlay device is used, television programming functions may still be provided by a television receiver that is not used to provide home automation functions.

Figure 3:
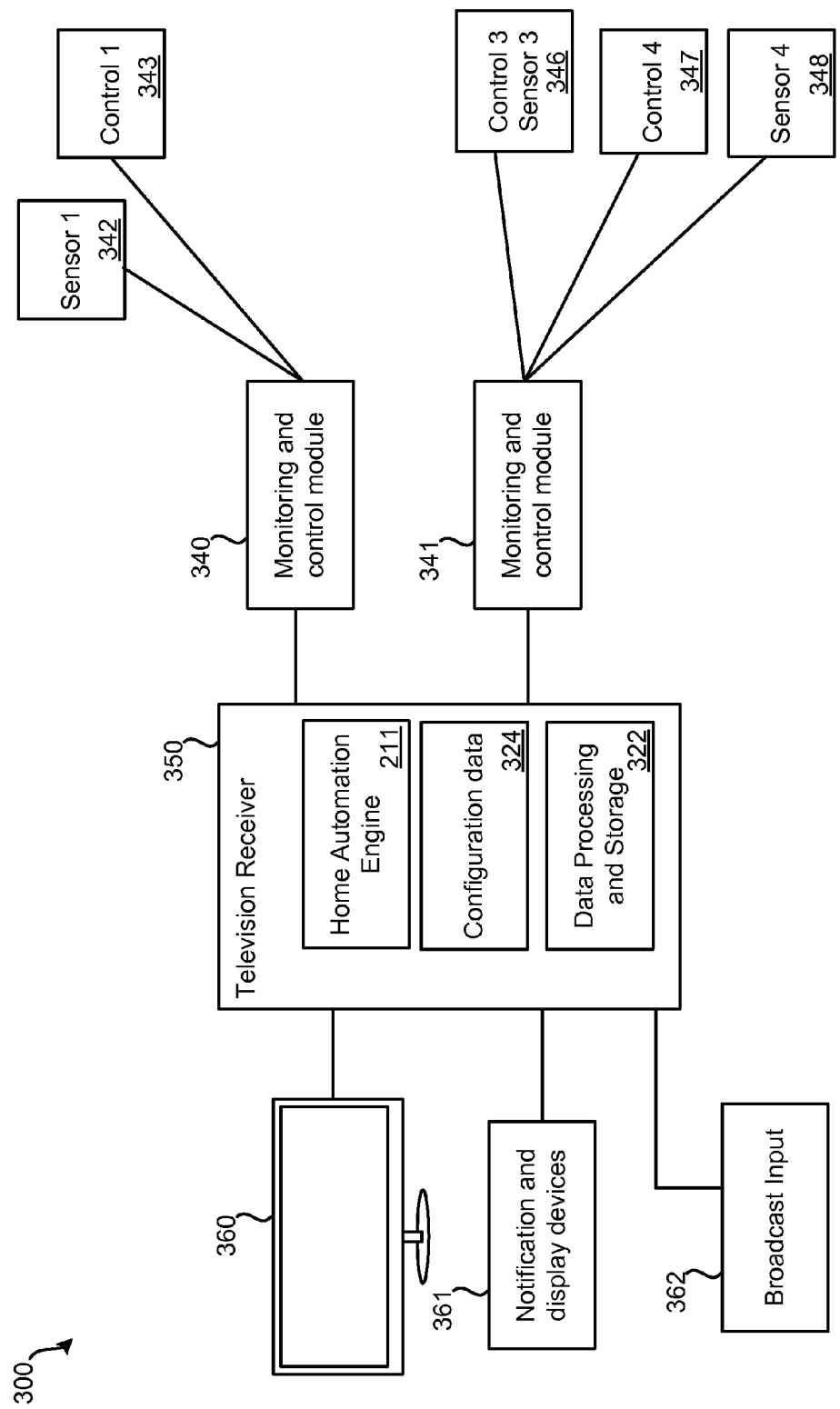
FIG. 3 illustrates an exemplary home automation system setup in accordance with embodiments of the present technology.

FIG. 3 shows an embodiment of a system for home monitoring and control that includes a television receiver 350. The system 300 may include a television receiver that is directly or indirectly coupled to one or more display devices 360 such as a television or a monitor. The television receiver may be communicatively coupled to other display and notification devices 361 such as stereo systems, speakers, lights, mobile phones, tablets, and the like. The television receiver may be configured to receive readings from one or more sensors 342, 348, or sensor systems 346 and may be configured to provide signals for controlling one or more control units 343, 347 or control systems 346.

In embodiments the television receiver may include a monitoring and control module 340, 341 and may be directly connected to or coupled to one or more sensors and/or control units. Sensors and control units may be wired or wirelessly coupled with the television receiver. The sensors and control units may be coupled and connected in a serial, parallel, star, hierarchical, and/or the like topologies and may communicate to the television receiver via one or more serial, bus, or wireless protocols and technologies which may include, for example, WiFi, CAN bus, Bluetooth, I2C bus, ZigBee, Z-Wave and/or the like.

The system may include one or more monitoring and control modules 340, 341 that are external to the television receiver 350. The television receiver may interface to sensors and control units via one or more of the monitoring and control modules. The external monitoring and control modules 340, 341 may be wired or wirelessly coupled with the television receiver. In some embodiments, the monitoring and control modules may connect to the television receiver via a communication port such as a USB port, serial port, and/or the like, or may connect to the television receiver via a wireless communication protocol such as Wi-Fi, Bluetooth, Z-Wave, ZigBee, and the like. The external monitoring and control modules may be a separate device that may be positioned near the television receiver or may be in a different location, remote from the television receiver.

In embodiments, the monitoring and control modules 340, 341 may provide protocol, communication, and interface support for each sensor and/or control unit of the system. The monitoring and control module may receive and transmit readings and provide a low level interface for controlling and/or monitoring the sensors and/or control units. The readings processed by the monitoring and control modules 340, 341 may be used by the other elements of the television receiver. For example, in some embodiments the readings from the monitoring and control modules may be logged and analyzed by the data processing and storage 322 module. The data processing and storage 322 module may analyze the received data and generate control signals, schedules, and/or sequences for controlling the control units. Additionally, the data processing and storage module 322 may utilize input data to generate additional outputs. For example, the module 322 may receive from a sensor 342 information from a communicatively coupled piece of exercise equipment. The sensor may be a part of or attached to the exercise equipment in various embodiments. The exercise equipment may provide information regarding the speed or mechanical movements associated with usage of the exercise equipment, and the data processing module 322 may use this data to generate relative distance information to be output to and displayed by display device 360. In some embodiments, the monitoring and control modules 340, 341 may be configured to receive and/or send digital signals and commands to the sensors and control units. The monitoring and control modules may be configured to receive and/or send analog signals and commands to the sensors and control units.

Sensors and control units may be wired or wirelessly coupled to the monitoring and control modules 340, 341 or directly or indirectly coupled with the receiver 350 itself. The sensors and control units may be coupled and connected in a serial, parallel, star, hierarchical, and/or the like topologies and may communicate to the monitoring and control modules via one or more serial, bus, or wireless protocols and technologies. The sensors may include any number of temperate, humidity, sound, proximity, field, electromagnetic, magnetic sensors, cameras, infrared detectors, motion sensors, pressure sensors, smoke sensors, fire sensors, water sensors, and/or the like. The sensors may also be part of or attached to other pieces of equipment, such as exercise equipment, or may be applications or other sensors as part of mobile devices.

The monitoring and control modules 340, 341 may be coupled with one or more control units. The control units may include any number of switches, solenoids, solid state devices and/or the like for making noise, turning on/off electronics, heating and cooling elements, controlling appliances, HVAC systems, lights, and/or the like. For example, a control unit may be a device that plugs into an electrical outlet of a home. Other devices, such as an appliance, may be plugged into the device. The device may be controlled remotely to enable or disable electricity to flow to the appliance. A control unit may also be part of an appliance, heating or cooling system, and/or other electric or electronic device such as a piece of exercise equipment. In embodiments the control units of other system may be controlled via a communication or control interface of the system. For example, the water heater temperature setting may be configurable and/or controlled via a communication interface of the water heater or home furnace. Additionally, the speed or other adjustment such as incline, resistance, on/off, etc. of a piece of exercise equipment may be controlled by an embedded control unit or module, or may be wired or wirelessly coupled with a monitoring and control module or the television receiver in order for such operational controls to be performed.

The controllers, e.g. Control 343, may include a remote control designed for association with the television receiver. For example, the receiver remote control device may be communicatively coupled with the television receiver, such as through interface 250, or one or more of the monitoring and control modules for providing control or instruction for operation of the various devices of the system. The control may be utilized to provide instructions to the receiver for providing adjustments to a piece of exercise equipment, for example, such that directional buttons of the remote may operate or be configured to adjust the piece of exercise equipment. For example, channel up or down, or selection buttons up and down, may be used to adjust resistance, speed, etc. of the piece of exercise equipment. The control may also be coupled with the piece of exercise equipment for modulation as well. For example, a USB port or wireless connection may be used to communicatively couple the piece of exercise equipment and the control to allow or provide the means for information transmission from the piece of equipment to the television receiver, as well as to provide the ability to operate or adjust the piece of equipment with the remote control.

Sensors may be part of other devices and/or systems. For example, sensors may be part of a mobile device such as a phone. The telemetry readings of the sensors may be accessed through a wireless communication interface such as a Bluetooth connection from the phone. As another example, temperature sensors may be part of a heating and ventilation system of a home. The readings of the sensors may be accessed via a communication interface of the heating and ventilation system. Sensors and/or control units may be combined into assemblies or units with multiple sensing capabilities and/or control capabilities. A single module may include, for example a temperature sensor and humidity sensor. Another module may include a light sensor and power or control unit and so on.

In embodiments, the sensors and control units may be configurable or adjustable. In some cases the sensors and control units may be configurable or adjustable for specific applications. The sensors and control units may be adjustable by mechanical or manual means. In some cases the sensors and control units may be electronically adjustable from commands or instructions sent to the sensors or control units. For example, the focal length of a camera may be configurable in some embodiments. The focal length of a camera may be dependent on the application of the camera. In some embodiments the focal length may be manually set or adjusted by a moving or rotating a lens. In some embodiments the focal length may be adjusted via commands that cause an actuator to move one or more lenses to change the focal length. In other embodiments, the sensitivity, response, position, spectrum and/or like of the sensors may be adjustable.

During operation of the system 300, readings from the sensors may be collected, stored, and/or analyzed in the television receiver 350. In embodiments, analysis of the sensors and control of the control units may be determined by configuration data 324 stored in the television receiver 350. The configuration data may define how the sensor data is collected, how often, what periods of time, what accuracy is required, and other characteristics. The configuration data may specify specific sensor and/or control unit settings for a monitoring and/or control application. The configuration data may define how the sensor readings are processed and/or analyzed. For example, for some applications, sensor analysis may include collecting sensor readings and performing time based analysis to determine trends, such as calories burned in total, over time, and during particular intervals. Such trending information may be developed by the receiver into charts or graphs for display to the user. For other applications, sensor analysis may include monitoring sensor readings to determine if a threshold value of one or more sensor has been reached.

The function of the system may be determined by loading and/or identifying configuration data for an application. In embodiments, the system 300 may be configured for more than one monitoring or control operation by selecting or loading the appropriate configuration data. In some embodiments the same sensors and/or control units may be used for multiple applications depending on the configuration data used to process and analyze sensor readings and/or activate the control units. Multiple monitoring and/or control applications may be active simultaneously or in a time multiplexed manner using the same or similar set of sensors and/or control units.

For example, the system 300 may be configured for both exercise monitoring and temperature monitoring applications using the same set of sensors. In embodiments, both monitoring applications may be active simultaneously or in a time multiplexed manner depending on which configuration data is loaded. In both monitoring applications the same sensors, such as proximity sensors, or cameras may be used. In the exercise monitoring application, data from the sensors may be gathered and recorded. The data may be analyzed to determine trends in fitness for the user. Statistics may be calculated regarding the user activity, movement, locations, and the like. Using the same sensors, the system may be configured for space temperature monitoring. For temperature monitoring the system may only monitor a specific subset of the sensors for activity. For temperature monitoring, sensor activity may not need to be saved or recorded. The sensor readings may be monitored for specific thresholds which may indicate a threshold temperature for adjusting the space temperature. In this example, the two different monitoring examples may be selected based on the active configuration data. When one configuration data is active, data from the sensors may be saved and analyzed for fitness monitoring. When the second configuration data is active, the system may monitor sensor readings for specific thresholds. Of course, multiple or alternative sensors may be used as well.

In embodiments the results, status, analysis, and configuration data details for each application may be communicated to a user. In embodiments auditory, visual, and tactile communication methods may be used. In some cases a display device such as a television may be used for display and audio purposes. The display device may show information related to the monitoring and control application. Statistics, status, configuration data, and other elements may be shown. Users may also save particular configuration data for devices, such as exercise equipment and/or other devices. A user may log in or be recognized by the system upon activation or beginning a particular workout and the system may make adjustments based on predetermined or recorded configuration data. For example, an enabled piece of exercise equipment may include a treadmill. A particular user may get on the device and using the control for the device, or using the receiver remote control, e.g. 343, may access a profile for the user. That profile may include that the user would begin training at a particular speed on the treadmill, and would want to watch a particular television channel while exercising, such as a 24 hour news program, or a particular piece of on-demand programming. The user may access the profile and select to begin, the user may be recognized by the system, or a combination such as being recognized by the system such that the television operations are performed or are input by a remote control, while the user himself selects a particular speed on the treadmill may occur.

Any number of additional adjustments or operations may be performed as well, as would be understood as encompassed by the present technology. For example, the space temperature may be monitored or adjusted as well. In one situation, after the user has been exercising for a period of time, generated heat may raise the space temperature above a threshold such that the home automation engine 211 additionally begins operation or adjustment of the HVAC system to cool the space. Additionally, configuration data for the user may include reducing the space temperature to a particular degree based on a preference of the user. Thus, when the user loads a profile or begins exercising, the home automation system may automatically begin adjusting the space temperature as well in anticipation of heat generation or user preferences.

In embodiments the system may include additional notification and display devices 361 capable of notifying the user, showing the status, configuration data, and/or the like. The additional notification and display devices may be devices that are directly or indirectly connected with the television receiver. In some embodiments computers, mobile devices, phones, tablets, exercise equipment, and the like may receive information, notifications, control signals, etc., from the television receiver. Data related to the monitoring and control applications and activity may be transmitted to remote devices and displayed to a user. Such display devices may be used for presenting to the user interfaces that may be used to further configure or change configuration data for each application. An interface may include one or more options, selection tools, navigation tools for modifying the configuration data which in turn may change monitoring and/or control activity of an application. Modification to a configuration may be used to adjust general parameters of a monitoring application to specific constraints or characteristics of a home, user's schedule, control units, and/or the like.

Display interfaces may be used to select and/or download new configurations for monitoring and/or control applications. A catalog of pre-defined configuration data definitions for monitoring and control applications may be available to a user. A user may select, load, and/or install the applications on the television receiver by making a selection using in part the display device. For example, a user may load a profile based on exercise habits as discussed above. In embodiments, configuration data may be a separate executable application, code, package, and/or the like. In some cases, the configuration data may be a set of parameters that define computations, schedules, options, for other processor executable code or instructions. Configuration data may be a meta data, text data, binary file, and/or the like.

In embodiments notification and display devices may be configured to receive periodic, scheduled, or continuous updates for one or more monitoring and control applications. The notifications may be configured to generate pop-up screens, notification banners, sounds, and/or other visual, auditory, and/or tactile alerts. In the case where the display device is a television, some notifications may be configured to cause a pop-up or banner to appear over the programming or content being displayed, such as a heart rate that reaches a dangerous threshold such as greater than 90% of a calculated max heart rate for a particular user. Such an alert may be presented in a centrally located box or in a position different from the fitness information to make it more recognizable. Additionally the program being watched can be paused automatically while such an alert is being presented, and may not be resumed unless receiving an input or acceptance from the user. Some notifications may be configured to cause the television to turn on if it is powered off or in stand-by mode and display relevant information for a user. In this way, users with health risks can be notified during exercise or other events based on monitoring that is being performed.

The television receiver may also be configured to receive broadcast or other input 362. Such input may include television channels or other information previously described that is used in conjunction with the monitoring system to produce customizable outputs. For example, a user may wish to watch a particular television channel while also receiving information or updates regarding a fitness activity being monitored. The television receiver may receive both the fitness information and television channel information to develop a modified output for display. The display may include a split screen in some way, a banner, an overlay, etc. Such operations for a fitness overlay or incorporation will be described in further detail below.

Figure 4:
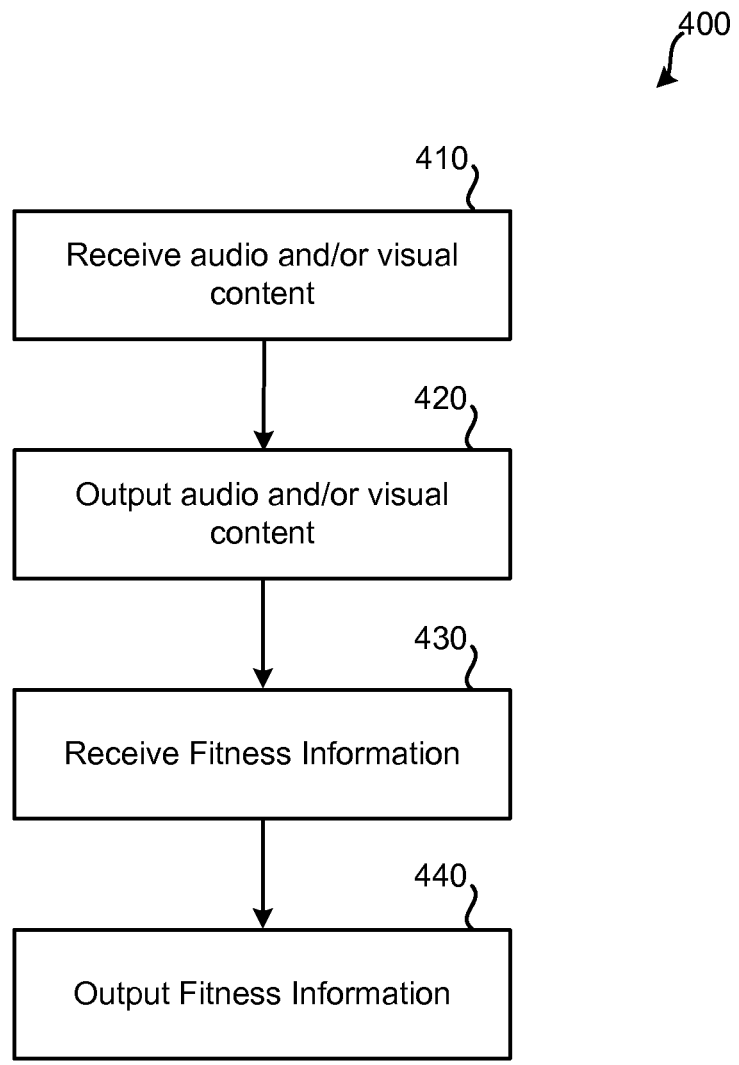
FIG. 4 shows a simplified flow diagram of a method of displaying fitness information according to embodiments of the present technology.

The systems and devices previously described may be used in performing various methods. The methods may also be represented by programming stored in memory of a computing device. FIG. 4 illustrates an embodiment of a method 400 for displaying fitness information and operating fitness equipment in conjunction with a home automation system. Method 400 may be performed using any of the systems or components previously described. Method 400 may allow for an electronic device to receive and display fitness information. Each step of method 400 may be performed at or by a single electronic device, such as an STB, television receiver, computer, or mobile device, for example, or by multiple devices communicating with one another. Means for performing each step of method 400 include an electronic device and/or the various components of an electronic device or distribution system, such as those detailed in relation to FIGS. 1 and 2. Method 400 may be performed using a computerized device, such as a device incorporating some or all of the components of computer system 600 of FIG. 6.

The method may include receiving audio and/or visual content at an input of the electronic device at operation 410. The content, including multimedia content, may include television information as previously described. The content or an aspect of the content, such as a particular channel, may be output to the display device at operation 420. Such an operation may be automatic, such as based on configuration data or a particular user profile as explained above, or may be based on a received input at the electronic device. The method may also include receiving fitness information at the electronic device at operation 430, which may be received in any number of ways as described below. The method may still include providing the fitness information to the display device at operation 440. The fitness information may be output together or separately from the multimedia or audio-visual content, and in one example may be output as an overlay on the multimedia content.

The fitness information may be received at the electronic device from one or more sources, which may include from an exercise device and/or a mobile device, which may include a mobile phone. When fitness information is received from the electronic device, it may be received directly from the device, which may be communicatively coupled with the electronic device. The electronic device may be enabled to operate within the particular home automation system as described above, such that the exercise device may be wired or wirelessly coupled with the system in a plug-and-play fashion, or such that it is recognized and information can be directly received from the device. Additionally, the exercise device may be wired or wirelessly coupled with a remote control associated with the electronic device to provide the fitness information. For example, a remote control for the electronic device, which may be a television receiver as described previously, may include a USB or other wired input that may be coupled with an output from the exercise device. In this way, the device may receive fitness or control information from the exercise device and provide it to the electronic device for use and display.

The present technology may be utilized with both technically advanced as well as relatively simple exercise devices. For example, a device enabled with the present system may be capable of providing a variety of fitness information for the system to use and display, as well as receiving a variety of controls from the system. Additionally, devices that may not be enabled, but may include an output capability may be incorporated with the automation system described to provide an amount of relevant fitness information, but may or may not be able to receive commands from the system or controllers, and may require manual or other input from a user. Still further, relatively simple exercise devices that include no input or output, or relatively crude input, may be utilized with additional devices that can be incorporated with the present system. For example, sensors may be attached to the device, or a mobile phone may be used to receive fitness information for incorporation with the system.

A mobile device, including a mobile phone, may be used to provide some of all of the fitness information as noted above. For example, the mobile device may have the functionality of a pedometer, and may be able to record steps of a user and/or speed of a user on a treadmill. Additionally, the phone may be communicatively coupled with sensors utilized by the user to acquire additional fitness information. For example, the mobile phone or device may be coupled with a heart rate monitor to receive information, and may be capable of receiving particular data about the user, such as height, weight, age, etc., to develop additional fitness information. Additionally, a sensor monitored by the system or mobile device may be coupled with an exercise device, such as a wheel or spinning mechanism of a bike or rowing machine to retrieve speed or other movement based information for use or display by the system.

The fitness information may include any amount or type of information receivable by the system. The fitness information may include vital statistics of a user such as heart rate, weight, age, gender, etc. The fitness information may also include any type of information related to the activity itself such as operational information about the exercise device, which may include speed, distance, resistance, incline/decline, etc. The information may include or be used to develop or calculate additional fitness information by the exercise device or the electronic device. Such information may include calories burned, relative distance traveled, and other statistical information which would be understood as encompassed by this technology.

The received or generated fitness information may be output for display on a display device with, as a combined output, or in addition to the audiovisual content. The audiovisual content may or may not be related to the fitness information. For example, the multimedia content may include an exercise bike-based or spinning video. The displayed information may be related to the content because the user is performing the activity shown in the video. Additionally, the user may be watching any multimedia content, such as a news program that is unrelated to the fitness information being displayed.

Display of the fitness information may include any number of display techniques including picture-in-picture, split screen or in a dedicated portion of the display device, or an overlay on the audiovisual content including a table or banner, including a scrolling banner, displaying the information. The fitness information may be received and/or displayed automatically, based on user profiles or presets, based on system configurations, or the information may be displayed or even provided in response to a control signal received from a mobile device or remote control associated with the electronic device. The displayed information may also be scrolled or adjusted to additional fitness information in response to user input, such as with a remote control or mobile device. In this way, the user can minimize the space of the banner, overlay, or portion of the screen dedicated to the fitness information if desired.

The electronic device may also be capable of controlling the exercise device either directly or indirectly, and the user may provide control signals to the electronic device by any number of means. The electronic device may receive an input from a remote control or mobile device associated with the electronic device. In response, the electronic device may provide a control signal from the electronic device to an exercise device to adjust operation of the exercise equipment device commensurate with the received input.

For enabled exercise devices, such functionality may allow the user to control the device with the same remote used to control the electronic device, e.g. the television remote. The remote may include generic buttons that may be used to operate the exercise device, or may additionally be configured such that buttons that perform one function during regular operation perform an additional or alternative function during exercise. For example, after a user has set a channel for viewing during an exercise activity, the user may program or the system may automatically reconfigure the channel up and down controls to resistance or speed controls of the electronic device. Additionally, the user may configure the buttons or different buttons to operate as such controls. For example, if a user knows he is likely to change the channel but not the volume during exercise, he may configure, or have profile or preset configurations adjusting the volume buttons to operate to adjust features of the exercise device. Of course, such controls can be configured, adjusted, or readjusted or reprogrammed at any time, such as through a menu interface of the system.

Such configurations may be enabled automatically by the system when the device is used. For example, a user may own multiple pieces of exercise equipment that are incorporated with the automation system, e.g. a treadmill and a rowing machine. A user may turn on one of the exercise devices at the device, with a remote, or with the system, and the act of engaging the exercise device may load configuration data for the remote. For example, the user may turn on the treadmill, and the system may at that time, based on recognition of the device, automatically configure buttons of the remote control to act as treadmill speed up/down controls. The user may then finish using the treadmill and decide to use the rowing machine, and the system may then automatically adjust the same buttons on the remote control to then operate as resistance up/down controls for the rowing machine. In embodiments all devices may be in an on or standby condition at all times. In such a situation, for example, the remote control may be reconfigured based on which device is currently in operation. Additionally, the electronic device may display a prompt on the screen requesting input from the user as to which device the remote control should be configured. In this way, multiple household members may be able to use exercise devices at the same time, and the person holding the remote control can utilize the remote for that piece of equipment as well as general system functions.

The home automation system can also perform additional or alternative home automation functions during the fitness activity, and may perform them either upon receiving user input, based on user profile information, or based on receiving additional information from the home automation system. For example, the electronic device may be receiving additional information from additional sensors during the fitness activity, in accordance with previously described functions, which may include temperature sensor readings or information for the house, and perhaps for the specific space in which the fitness activity is occurring. The electronic device may determine that the temperature of any space associated with the electronic device, such as the space in which the fitness activity is occurring has changed. For example, as the fitness activity continues, the space temperature, if not the house temperature, may increase over time. This temperature change may reach a threshold, or may be occurring at a rate such that the electronic device determines to operate the HVAC system. In particular, the electronic device may provide a control signal to a communicatively coupled heating or air conditioning system to adjust the temperature of the house or space. For systems in which automated window and/or door controls are included, the system may instead automatically open a window of the fitness space or elsewhere. Such a determination may be made based on preprogrammed information, or collected information including outside temperature.

Additionally, such temperature control may be a part of a user profile or configuration information. For example, if a user is recognized by the system or provides a selection to a particular user profile for a piece of exercise equipment, the profile may include adjustments to space temperature for the fitness area or for the house in general. In this way, increases in space temperature associated with fitness activity can be virtually anticipated such that the cooling system need not attempt to catch up once a threshold is reached, and possibly exceeded before the system can regulate the temperature. Any number of additional or alternative functionalities can be provided by the described home automation system that would be understood by the skilled artisan and are encompassed by the present technology.

Figure 5:
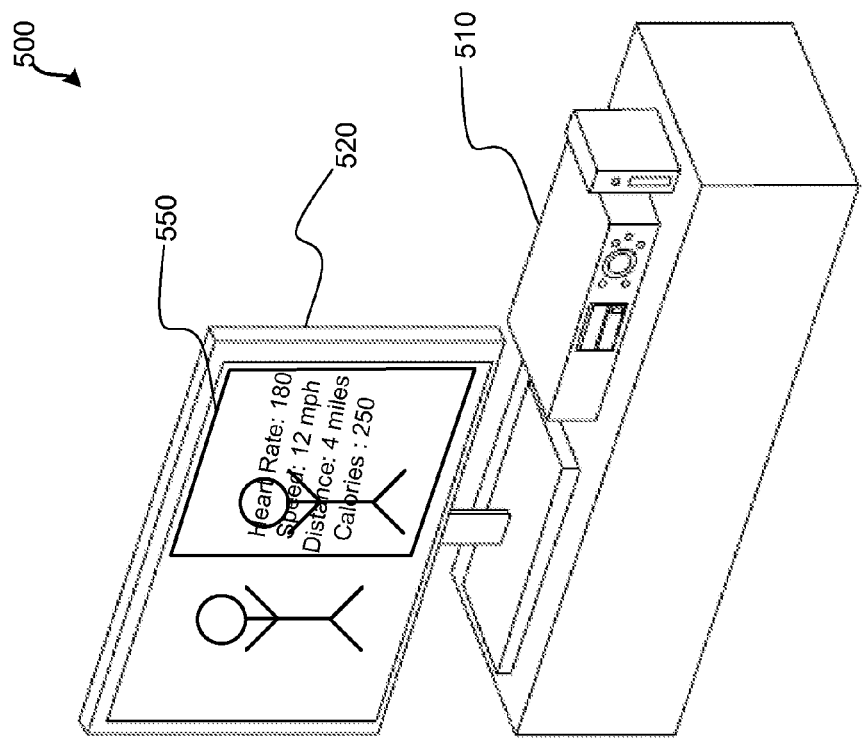
FIG. 5 illustrates an exemplary overlay of fitness information according to the present technology.
Figure 5:
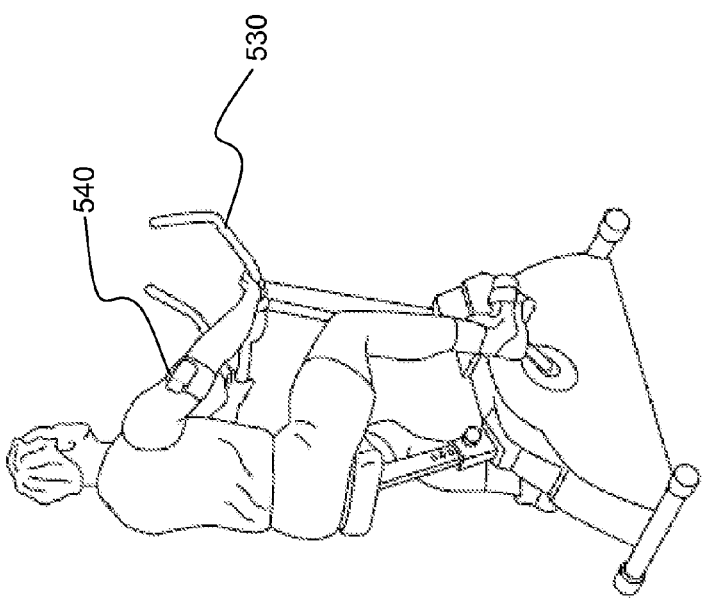

FIG. 5 illustrates an example of a user interfacing with and utilizing the fitness overlay and incorporation of the present technology with an exemplary exercise device. The illustrated device 530 does not include an informational display, but such devices can readily be incorporated with the system as described above. System 500 includes an electronic device 510 as previously described, which may be an STB or television receiver. The device is communicatively coupled with a television 520, although any previously described display device may be used.

The user of system 500 is using exercise device 530, e.g. an exercise bike, while watching television, a movie, or some type of multimedia content. Exercise device 530 may include no or limited display capabilities for providing fitness information. The user, however, may be utilizing mobile device 540 for acquiring fitness information. Mobile device 540 may be a mobile phone or other device that can be maintained by the user in a variety of locations. For example, device 540 is illustrated on a band on the user's arm, but may be in his pocket, or otherwise located near or on the user. The device may have incorporated functionalities, such as a pedometer function, so for treadmill devices, it may record steps, etc. Additionally, the mobile device 540 may be in communication with one or more additional sensors to receive fitness information. Mobile device 540 may be in communication with a watch or sensor that records heart rate information, and the mobile device may also be configured to include information about the user including age, gender, weight, etc. The mobile device may be capable of generating additional fitness information with this information, or may merely transmit the information to the electronic device 510 for use.

Additional sensors (not shown) may also be coupled with the exercise device 530 to retrieve additional fitness information. The sensor may be coupled with a wheel or mechanical device of the exercise device 530 to collect speed and/or distance type information from the device. Such a sensor may be associated with mobile device 540 or the electronic device 510 to provide the gathered information.

The information retrieved by electronic device 510 may be used to develop or provide fitness information for display on television 520. For example, electronic device 510 may be receiving the television information or transmission from an alternative input than the fitness information, and may output these streams as a combined stream or as multiple streams. The fitness information is illustrated as an overlay 550 on the television 520, but may be presented in any number of ways as previously described, that may also be adjusted by the user during transmission. The fitness information includes information both received from the mobile device 540, as well as information generated by the mobile device 540 or electronic device 510, e.g. calories burned or relative distance traveled. By displaying the information directly on the television or display device being watched by the user, the user is able to examine the fitness information without having to access the mobile device, which may not be in a visibly accessible location. Additionally, fitness information may still be determined and provided to the user despite that the exercise device 530 may have no capabilities for displaying information to a user itself. Additionally, embodiments in which a mobile device is used may also allow the mobile device to perform other control functions for the system such that the user may not need to maintain an additional control device while exercising. For example, the mobile device may utilize an application that provides receiver functionality on the phone itself. As would be understood, any number of other incorporation schemes can be utilized including a variety of different exercise devices, communication means and abilities, and display overlays, all of which are encompassed by the present technology.

Figure 6:
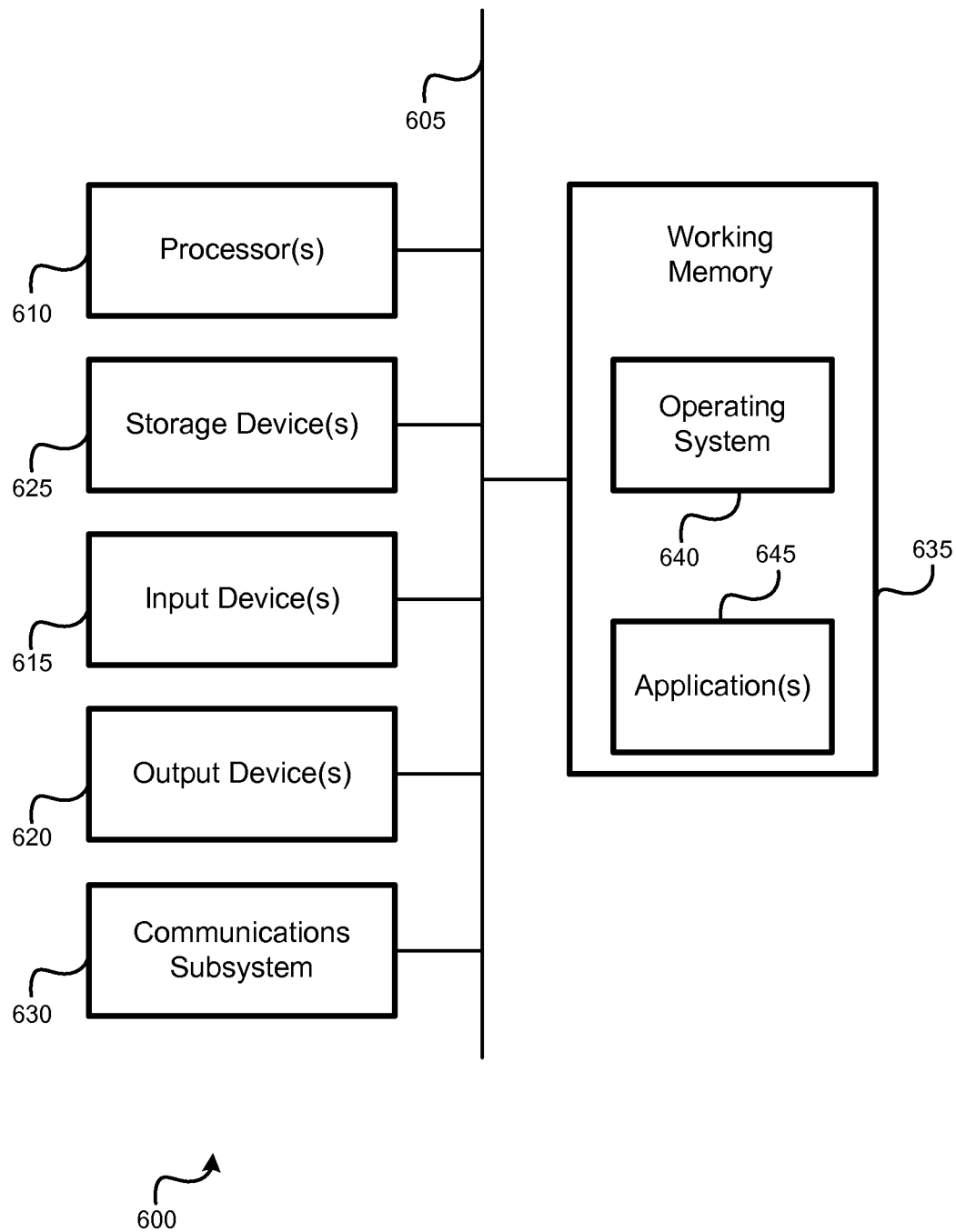
FIG. 6 shows a simplified computer system that may be utilized to perform one or more of the operations discussed.

FIG. 6 illustrates an embodiment of a computer system 600. A computer system 600 as illustrated in FIG. 6 may be incorporated into devices such as an STB, a first electronic device, DVR, television, media system, personal computer, and the like. Moreover, some or all of the components of the computer system 600 may also be incorporated into a portable electronic device, mobile phone, or other device as described herein. FIG. 6 provides a schematic illustration of one embodiment of a computer system 600 that can perform some or all of the steps of the methods provided by various embodiments. It should be noted that FIG. 6 is meant only to provide a generalized illustration of various components, any or all of which may be utilized as appropriate. FIG. 6, therefore, broadly illustrates how individual system elements may be implemented in a relatively separated or relatively more integrated manner.

The computer system 600 is shown comprising hardware elements that can be electrically coupled via a bus 605, or may otherwise be in communication, as appropriate. The hardware elements may include one or more processors 610, including without limitation one or more general-purpose processors and/or one or more special-purpose processors such as digital signal processing chips, graphics acceleration processors, and/or the like; one or more input devices 615, which can include without limitation a mouse, a keyboard, a camera, and/or the like; and one or more output devices 620, which can include without limitation a display device, a printer, and/or the like.

The computer system 600 may further include and/or be in communication with one or more non-transitory storage devices 625, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 600 might also include a communications subsystem 630, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 630 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 630. In other embodiments, a portable electronic device, e.g. the first electronic device, may be incorporated into the computer system 600, e.g., an electronic device or STB, as an input device 615. In many embodiments, the computer system 600 will further comprise a working memory 635, which can include a RAM or ROM device, as described above.

The computer system 600 also can include software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 4, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code might be stored on a non-transitory computer-readable storage medium, such as the storage device(s) 625 described above. In some cases, the storage medium might be incorporated within a computer system, such as computer system 600. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 600 and/or might take the form of source and/or installable code, which, upon compilation and/or installation on the computer system 600 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 600 to perform methods in accordance with various embodiments of the technology. According to a set of embodiments, some or all of the procedures of such methods are performed by the computer system 600 in response to processor 610 executing one or more sequences of one or more instructions, which might be incorporated into the operating system 640 and/or other code, such as an application program 645, contained in the working memory 635. Such instructions may be read into the working memory 635 from another computer-readable medium, such as one or more of the storage device(s) 625. Merely by way of example, execution of the sequences of instructions contained in the working memory 635 might cause the processor(s) 610 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 600, various computer-readable media might be involved in providing instructions/code to processor(s) 610 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 625. Volatile media include, without limitation, dynamic memory, such as the working memory 635.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 600.

The communications subsystem 630 and/or components thereof generally will receive signals, and the bus 605 then might carry the signals and/or the data, instructions, etc. carried by the signals to the working memory 635, from which the processor(s) 610 retrieves and executes the instructions. The instructions received by the working memory 635 may optionally be stored on a non-transitory storage device 625 either before or after execution by the processor(s) 610.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. An electronic device comprising:
   a first input component configured to receive multimedia data;
   a second input component configured to receive fitness information;
   at least one output component communicatively coupled with at least one display device;
   one or more processors; and
   memory communicatively coupled with and readable by the one or more processors and having stored therein processor-readable instructions, which when executed by the one or more processors cause the one or more processors to:
   receive multimedia content through the first input component;
   provide the multimedia content through the at least one output;
   receive fitness information through the second input component; and
   provide the fitness information through the at least one output component.

2. The electronic device of claim 1, wherein the fitness information is received from a communicatively coupled exercise device.

3. The electronic device of claim 1, wherein the electronic device further comprises a remote control communicatively coupled with both the electronic device and the exercise device.

4. The electronic device of claim 1, wherein the fitness information is received from a communicatively coupled mobile device configured to acquire the fitness information.

5. The electronic device of claim 1, wherein the electronic device comprises a television receiver.

6. The electronic device of claim 1, wherein the processors are further caused to combine the received fitness information with the multimedia content as a single output.

7. The electronic device of claim 1, wherein the processors are further caused to receive temperature information from communicatively coupled temperature sensors.

8. The electronic device of claim 7, wherein the processors are further caused to determine, based on the received temperature information, that the temperature of a space associated with the electronic device has changed.

9. The method of claim 8, wherein the processors are further caused to provide a control signal to a heating or air conditioning device to adjust the temperature of the space.

* * * * *